United States Patent
Nakamura

(10) Patent No.: US 9,295,415 B2
(45) Date of Patent: Mar. 29, 2016

(54) FOREIGN OBJECT DETERMINATION DEVICE, FOREIGN OBJECT DETERMINATION METHOD AND FOREIGN OBJECT DETERMINATION PROGRAM

(75) Inventor: Yoichi Nakamura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 296 days.

(21) Appl. No.: 13/581,078

(22) PCT Filed: Mar. 2, 2011

(86) PCT No.: PCT/JP2011/054752
§ 371 (c)(1),
(2), (4) Date: Aug. 24, 2012

(87) PCT Pub. No.: WO2011/108582
PCT Pub. Date: Sep. 9, 2011

(65) Prior Publication Data
US 2012/0314918 A1  Dec. 13, 2012

(30) Foreign Application Priority Data
Mar. 4, 2010  (JP) ................. 2010-047585

(51) Int. Cl.
*G06K 9/00* (2006.01)
*A61B 5/117* (2006.01)

(52) U.S. Cl.
CPC .......... *A61B 5/1172* (2013.01); *G06K 9/00033* (2013.01); *G06K 9/00375* (2013.01)

(58) Field of Classification Search
None
See application file for complete search history.

(56) References Cited

U.S. PATENT DOCUMENTS

| 5,937,082 | A | 8/1999 | Funada | |
|---|---|---|---|---|
| 7,587,081 | B2 * | 9/2009 | Rovira-Mas et al. | 382/154 |
| 7,720,279 | B2 * | 5/2010 | Hayaishi | 382/164 |
| 8,270,726 | B2 * | 9/2012 | Niinuma et al. | 382/199 |
| 2006/0165264 | A1 * | 7/2006 | Saitoh et al. | 382/115 |
| 2008/0101664 | A1 * | 5/2008 | Perez | 382/125 |
| 2008/0211627 | A1 | 9/2008 | Shinzaki | |
| 2009/0087022 | A1 | 4/2009 | Fukuda et al. | |
| 2011/0200237 | A1 * | 8/2011 | Nakamura et al. | 382/127 |
| 2013/0162535 | A1 | 6/2013 | Nishida et al. | |

FOREIGN PATENT DOCUMENTS

| CN | 101256628 A | 9/2008 |
|---|---|---|
| CN | 101419498 A | 4/2009 |

(Continued)

OTHER PUBLICATIONS

English Abstract of Japanese Patent Publication No. JP 05-266174, dated Oct. 15, 1993.

(Continued)

*Primary Examiner* — Vikkram Bali
(74) *Attorney, Agent, or Firm* — Scully, Scott, Murphy & Presser, P.C.

(57) ABSTRACT

To improve the accuracy of fingerprint authentication, the foreign object determination device of the present invention includes an image acquisition unit 31 for acquiring an image in which an authentication target to be subjected to fingerprint authentication has been captured, a region partitioning unit 33 for partitioning the image acquired by the image acquisition unit 31 into regions of mutually different colors by using predetermined determination criteria for determining differences in color, and a foreign object determination unit 34 for determining whether a foreign object is included in the authentication target by using colors and/or areas of the regions partitioned by the region partitioning unit 33.

15 Claims, 3 Drawing Sheets

(56) References Cited

FOREIGN PATENT DOCUMENTS

| CN | 101460971 A | 6/2009 |
|---|---|---|
| JP | H 09-167230 A | 6/1997 |
| JP | 2000-011143 | 1/2000 |
| JP | 3100456 | 8/2000 |
| JP | 2002-177624 A | 6/2002 |
| JP | 2003-006645 | 1/2003 |
| JP | 2007-122237 | 5/2007 |

OTHER PUBLICATIONS

International Search Report dated Mar. 29, 2011 issued in PCT/JP2011/054752.

Extended European search report dated Sep. 29, 2014 received in related application EP 11750691.5.

Abdullah-Al-Wadud, M. et al., "Region-of-Interest Selection for Skin Detection Based Applications", Convergence Information Technology, 2007. International Conference on IEEE, Piscataway, NJ, Nov. 21, 2007, pp. 1999-2004, XP031225489, ISBN: 978-0-7695-3038-3.

Chinese Official Action dated Jun. 30, 2014 received in related application CN 201180012092.X together with an English language translation.

Chinese Official Action dated Feb. 27, 2015 received in related application CN 201180012092.X together with an English language translation.

* cited by examiner

FOREIGN OBJECT DETERMINATION DEVICE, FOREIGN OBJECT DETERMINATION METHOD AND FOREIGN OBJECT DETERMINATION PROGRAM

BACKGROUND

The present invention relates to a foreign object determination device, a foreign object determination method and a foreign object determination program.

Fingerprint authentication is attracting attention as one type of authentication system for identifying individuals. A fingerprint is unique in that it is different for every person, and that it does not change even with the lapse of time. Accordingly, it is said that fingerprint authentication is more reliable than the currently prevalent password authentication or the like. As a method of fingerprint authentication, for example, there is a method of performing fingerprint authentication by a finger mounted on a mounting surface being irradiated with light, and using a ridge-shaped pattern image of the fingerprint obtained by focusing and imaging, via an optical system, the reflected light that scatters due to the unevenness of the fingerprint (refer to Patent Document 1 below).

[Patent Document 1] Japanese Patent Publication No. 3100456

Meanwhile, with the fingerprint authentication described in foregoing Patent Document 1, when a foreign object such as a tape is attached to the fingertip, a proper ridge-shaped pattern image cannot be obtained and the fingerprint authentication cannot be performed appropriately.

SUMMARY

The present invention was devised to resolve the foregoing problem, and an object of this invention is to provide a foreign object determination device, a foreign object determination method and a foreign object determination program capable of improving the accuracy of fingerprint authentication.

The foreign object determination device of the present invention comprises an image acquisition unit for acquiring an image in which an authentication target to be subjected to fingerprint authentication has been captured, a region partitioning unit for partitioning the image acquired by the image acquisition unit into regions of mutually different colors by using predetermined determination criteria for determining differences in color, and a foreign object determination unit for determining whether a foreign object is included in the authentication target by using colors and/or areas of the regions partitioned by the region partitioning unit.

The foreign object determination method of the present invention comprises an image acquisition step of acquiring an image in which an authentication target to be subjected to fingerprint authentication has been captured, a region partitioning step of partitioning the image acquired in the image acquisition step into regions of mutually different colors by using predetermined determination criteria for determining differences in color, and a foreign object determination step of determining whether a foreign object is included in the authentication target by using colors and/or areas of the regions partitioned in the region partitioning step.

The foreign object determination program of the present invention causes a computer to execute the respective steps of the foregoing foreign object determination method.

According to the present invention, it is possible to improve the accuracy of fingerprint authentication.

DETAILED DESCRIPTION

The preferred embodiments of the foreign object determination device, the foreign object determination method and the foreign object determination program according to the present invention are now explained with reference to the appended drawings.

Figure 1:
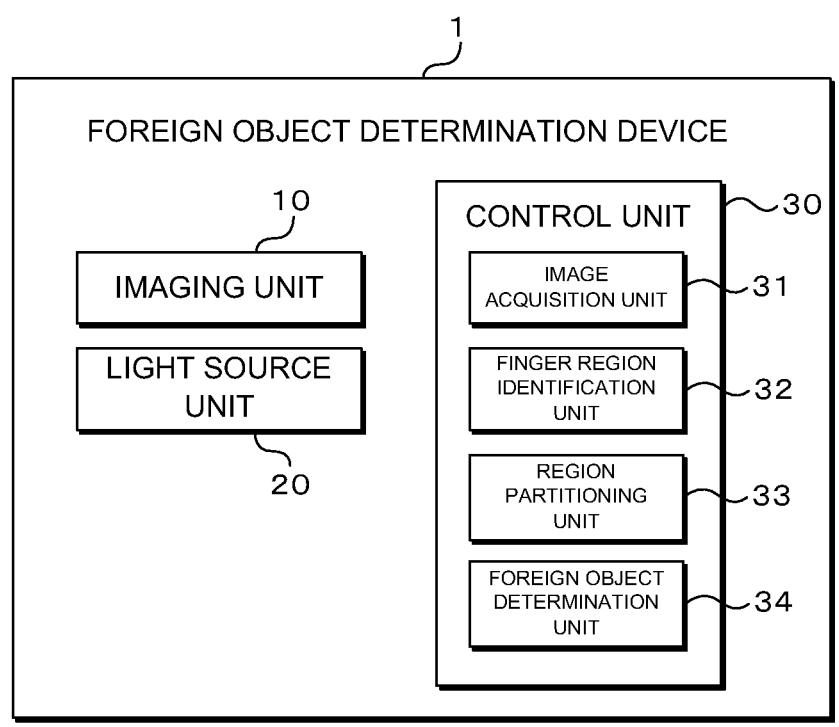
FIG. 1 is a block diagram illustrating the schematic configuration of the foreign object determination device in an embodiment of the present invention.

The schematic configuration of the foreign object determination device according to an embodiment of the present invention is foremost explained with reference to FIG. 1. FIG. 1 is a diagram schematically showing the configuration of the foreign object determination device. The foreign object determination device 1 is an apparatus for determining whether a foreign object is included in an authentication target to be subjected to fingerprint authentication. The foreign object determination device 1 performs fingerprint authentication when a foreign object is not included in the authentication target. The finger to be the authentication target is placed, for example, on a predetermined mounting region provided on the top surface of the foreign object determination device 1.

As shown in FIG. 1, the foreign object determination device 1 includes an imaging unit 10, a light source unit 20, and a control unit 30. The imaging unit 10 captures the authentication target placed on the mounting region. As the imaging unit 10, for instance, a camera and an image sensor may be used. The imaging unit 10 in this embodiment comprises a camera and an image sensor. The camera is disposed at a position where it is possible to capture an image containing both the finger and the foreign object when a foreign object exists on the fingerprint to undergo fingerprint authentication (hereinafter also referred to as the "image for foreign object determination"). The image sensor is disposed at a position where it is possible to capture an image of the finger containing the fingerprint portion required for fingerprint authentication (hereinafter also referred to as the "image for fingerprint authentication").

Note that the imaging unit 10 does not necessarily have to comprise both the camera and the image sensor. For example, the imaging unit 10 may also comprise one camera or one image sensor. In the foregoing case, the imaging unit 10 may capture a combined image of the image for foreign object determination and the image for fingerprint authentication with one camera or one image sensor.

The light source unit 20 is, for example, an LED (Light-Emitting Diode), and causes the authentication target to be irradiated with light when the authentication target is to be captured by the imaging unit 10.

Note that, as a general rule, the respective constituent elements of the imaging unit 10, the light source unit 20 and the control unit 30 provided to the foreign object determination device 1 are the same as the imaging unit, the light source unit and the control unit of a conventional fingerprint authentication apparatus. However, the foreign object determination device 1 of the present invention differs from a conventional fingerprint authentication apparatus with respect to the point that the control unit 30 of the foreign object determination device 1 includes various functions for determining the existence of a foreign object.

Moreover, the foreign object determination device 1 is physically configured by including a CPU, a memory, an imaging unit, and a light source unit. The memory includes, for example, a ROM storing programs and data to be processed by the CPU, and a RAM that is mainly used as the various work areas for performing control processing. These elements are mutually connected via a bus. As a result of the CPU executing the programs stored in the ROM and performing processing by using the image data captured by the imaging unit and the various types of data expanded in the RAM, it is possible to realize the functions of the respective parts in the foreign object determination device 1.

The control unit 30 controls the overall foreign object determination device 1 by executing the various types of control processing. The control unit 30 includes, for example, an image acquisition unit 31, a finger region identification unit 32, a region partitioning unit 33, and a foreign object determination unit 34.

The image acquisition unit 31 acquires, from the imaging unit 10, the two images for foreign object determination captured with the camera of the imaging unit 10. The two images for foreign object determination are images obtained by the camera of the imaging unit 10 capturing the same authentication target twice by shifting the photography timing.

The photography timing is set, for example, so that the first image is captured when the authentication target to undergo the fingerprint authentication is placed on the mounting surface, and the second image is captured when the authentication target moves slightly due to changes in the posture of the authentication subject after the first image has been captured. The second image may be captured, for example, after the lapse of a predetermined time after the first image has been captured. The foregoing predetermined time may be suitably set by obtaining, through testing, the time that the authentication target is assumed to start moving after the first image has been captured, and giving consideration to the value thereof. It is thereby possible to capture the image for foreign object determination in which the authentication target is captured before and after movement.

The finger region identification unit 32 identifies a finger region by using the two images for foreign object determination. The finger region identification unit 32 identifies the finger region, for example, according to the following procedures.

Foremost, the finger region identification unit 32 compares the colors of the two images for foreign object determination in pixel units. Specifically, the processing of comparing the colors of pixels positioned at the same coordinates of both images is performed with respect to all coordinates.

Subsequently, the finger region identification unit 32 identifies pixels in which the level of color change is a predetermined value or more as difference pixels. The predetermined value may be suitably set by obtaining, through testing, potential values upon the movement of the finger, and giving consideration to such values. Here, the precondition that the object that moves between the images for foreign object determination is a finger and a foreign object attached to the finger is satisfied. Accordingly, for example, by identifying the pixels that changed from the background color to the skin color or other colors (color of the foreign object) or the pixels that changed from the skin color or other colors to the background color, it is possible to identify the approximate position of the finger and the foreign object existing in the image for foreign object determination.

Subsequently, the finger region identification unit 32 identifies a flesh color pixel group corresponding to the skin color from the image for foreign object determination that was captured first. As the skin color, in an HSV (Hue, Saturation, Value), for instance, adopted may be a color where H is 0 or more and 40 or less or 320 or more and 360 or less, and V is 150 or more. In the foregoing case, red is set to 0 (360) to become the reference of H, and V is represented with a value between 0 and 255.

Subsequently, the finger region identification unit 32 identifies the finger region using the identified difference pixel group and flesh color pixel group. Accordingly, as a result of identifying the finger region by using the difference pixel group in addition to the flesh color pixel group, it is possible to identify, with greater accuracy, both the finger and foreign object from the image for foreign object determination even in cases where a foreign object of a color that is different from the skin color is attached to the finger. Moreover, when a region that is approximate to the skin color is included in the background, such region can be eliminated as noise.

The region partitioning unit 33 partitions the finger region identified by the image for foreign object determination into regions of mutually different colors by using colors of the respective pixels contained in the finger region.

Here, since the finger region is the region in which the finger was captured, under normal circumstances, the entire region should be a skin color. However, if a foreign object is attached to the finger, the color of the foreign object will get mixed into the finger region. Accordingly, in cases where a foreign object is attached to the finger, the finger region can be partitioned into a plurality of regions by partitioning the finger region for each different color. Meanwhile, if a foreign object is not attached to the finger, the possibility that the finger region will be partitioned is low.

As a method of partitioning the finger region into regions of mutually different colors, for example, the known partitioning methods of clustering or histogram may be used. Clustering may be hierarchical clustering or non-hierarchical clustering. As the hierarchical clustering, for example, there are the nearest neighbor method, the furthest neighbor method, the group average method, the barycentric method, and the like. As the non-hierarchical clustering, for example, there are the k-means method (k-average method), the k-medoids method, and the like.

Upon partitioning the finger region using the various partitioning methods described above, the region partitioning unit 33 partitions the finger region into regions of mutually different colors by using predetermined determination criteria. As the predetermined determination criteria, used is a reference for determining the difference in colors. A specific example upon partitioning the finger region using the predetermined determination criteria is now explained based on a representative partitioning method.

When using the nearest neighbor method as the hierarchical clustering, for example, the distance between the cluster in which the number of elements becomes greatest and the other clusters among the plurality of classified clusters is calculated. It is determined that the colors are mutually different when there is another cluster in which the calculated distance is a predetermined distance or greater, and the finger region is partitioned into a pixel group belonging to that other cluster and a pixel group belonging to the remaining clusters.

Here, the reason why the cluster in which the number of elements becomes greatest is used as the reference is explained below. Since most of the finger region is considered to be an image of a finger, the color of most of the finger region should be a color that is unique to that finger. Accordingly, by partitioning the finger region based on the cluster in which the number of elements becomes greatest, it is possible to partition the finger region into a finger portion and a non-finger portion.

When using the k-means method as the non-hierarchical clustering and classification into two clusters is performed, for example, it is determined that the colors are mutually difference when the distance between the two classified clusters is a predetermined distance or greater, and the finger region is partitioned into pixel groups belonging to the respective clusters.

Upon using a histogram, for example, the barycentric position is obtained from the histogram of the colors contained in the finger region. In addition, if there is a pixel group in which the distance from the barycentric position is a predetermined distance or greater, it is determined that the colors are mutually different in the foregoing pixel group and the pixel group in which the distance from the barycentric position is less than a predetermined distance, and the finger region is partitioned into the respective pixel groups.

Note that the respective predetermined distances described above may be suitably set by obtaining, through testing, potential values between the finger and the foreign object, and giving consideration to such values.

The foreign object determination unit 34 determines whether a foreign object is included in the authentication target by using the colors and areas of the partitioned regions that were partitioned by the region partitioning unit 33. The foreign object determination unit 34 determines the existence of a foreign object, for instance, according to the following procedures.

Foremost, the foreign object determination unit 34 obtains the barycentric position from the histogram of the colors contained in the finger region. Subsequently, the foreign object determination unit 34 calculates a score showing the difference in color in comparison to the barycentric position for each pixel of the partitioned regions. The score, for example, is calculated to be a larger value as the distance from the barycentric position is greater in the histogram. Consequently, the score will take on a larger value as the difference in color in comparison to the barycentric position is greater.

Here, under normal circumstances, the barycentric position should be the color of the finger as the authentication target. Accordingly, the score of pixels of the finger portion will be a value that is approximate to 0. Meanwhile, the score of pixels of the foreign object portion attached to the finger will be a larger score as the difference in color in comparison to the skin color is greater.

Note that the color to be used as the reference upon calculating the score is not limited to the foregoing barycentric position. For example, the reference may also be the average value of the colors contained in the finger region. Moreover, it is also possible to calculate only the score of the representative pixels of the partitioned regions without calculating the score of all pixels of the partitioned regions. As the representative pixels, for example, it is also possible to use the pixels corresponding to the average value of the colors of the partitioned regions or the colors of the barycentric position.

Subsequently, the foreign object determination unit 34 adds up the scores, which were calculated for each pixel, for each partitioned region. As a result of adding up the scores for each partitioned region, it is possible to improve the accuracy of foreign object determination in comparison to the case of calculating only the score of the representative pixels of the partitioned regions. This is because, if the color of the foreign object is similar to the color of the finger, the difference between the score of the representative pixels of the foreign object portion and the score of the representative pixels of the finger portion will decrease, and, by adding up the scores for each partitioned region, the difference between the two can be increased according to the areas of the partitioned regions. In other words, when determining the existence of a foreign object, by giving consideration to the colors and areas of the partitioned regions, the difference in colors for each partitioned region can be represented more notably as the areas of the partitioned regions are larger.

Subsequently, the foreign object determination unit 34 determines that a foreign object is included in the authentication target when any of the scores added up for each partitioned region are greater than a predetermined value by which the foreign object is assumed to exist. The foregoing predetermined value may be suitably set by obtaining, through testing, potential values that may be calculated as a foreign object, and giving consideration to such values.

Note that, when determining the existence of a foreign object, it is not necessary to use both the colors and areas of the partitioned regions. The existence of a foreign object can also be determined by using either the colors or areas of the partitioned regions. When using the colors of the partitioned regions, for example, it is possible to obtain the barycentric position of the colors for each of the partitioned regions, and determine that a foreign object is included in the authentication target when the distance between the respective barycentric position is greater than a predetermined distance.

Meanwhile, when using the areas of the partitioned regions, for example, it is possible to determine that a foreign object is included in the authentication target when there are a plurality of areas that are larger than the smallest area in which a foreign object is assumed to exist among the areas of the partitioned regions. Moreover, if a foreign object is not included in the authentication target, based on the premise that the finger region will not be partitioned, for instance, it is also possible to determine that a foreign object is included in the authentication target when there are a plurality of partitioned regions with an area.

Moreover, in the present invention, since it will suffice if it is possible to determine whether a foreign object is on a finger, there is no need to differentiate which partitioned region corresponds to the finger among the plurality of partitioned regions, and which partitioned region corresponds to the foreign object. For example, when most of the finger is covered by a foreign object, the barycentric position of the histogram of the colors contained in the foregoing finger region will be the color of the foreign object. In the foregoing case, the score of pixels of the foreign object portion will be a value that is approximate to 0, and the score of pixels of the finger portion will be a large value. In addition, since the added scores of pixels of the finger portion will be greater than a predetermined value, it is determined that a foreign object is included in the authentication target.

Figure 2:
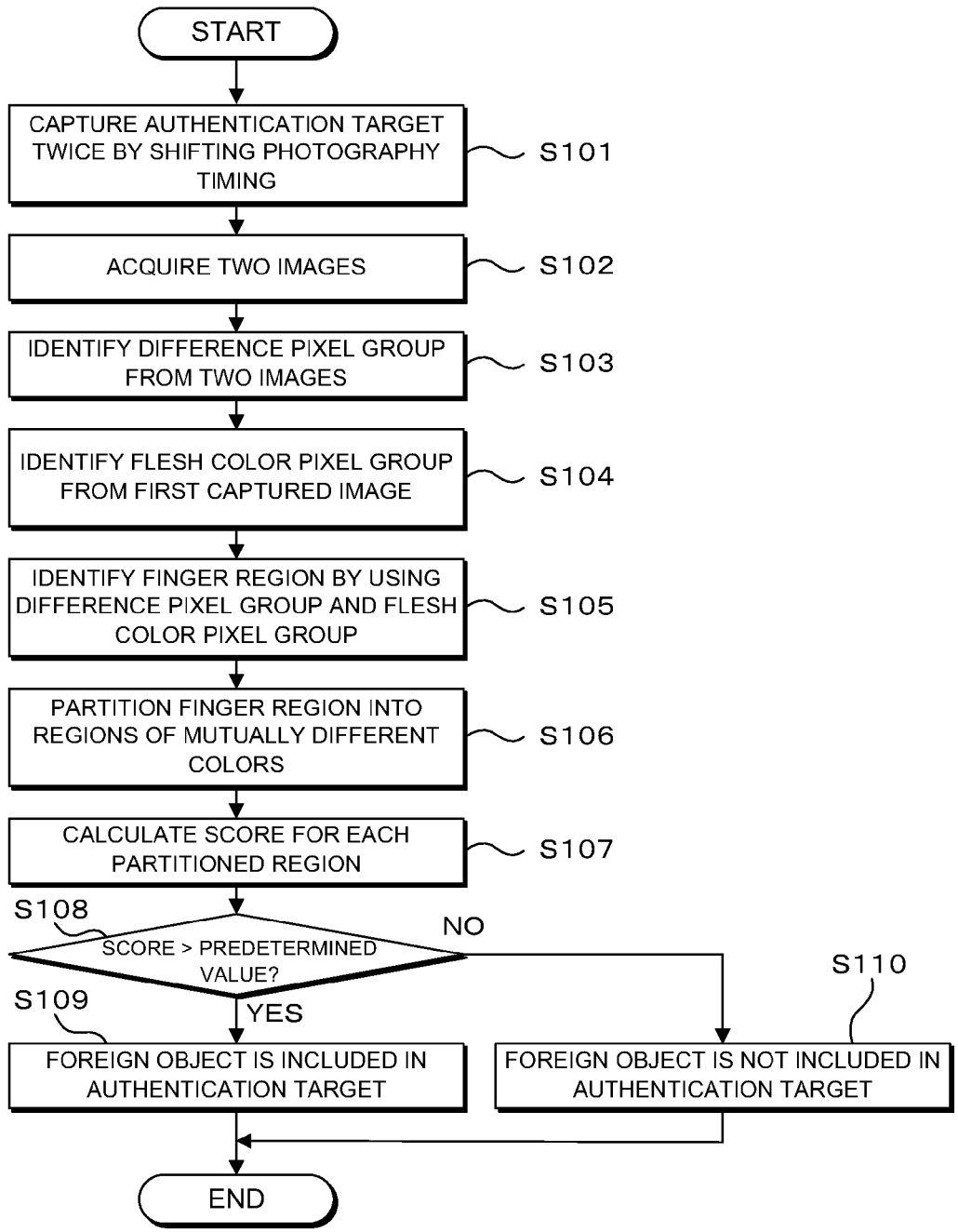
FIG. 2 is a flowchart illustrating the processing routine in determining the existence of a foreign object in an authentication target.

The foreign object determination processing to be executed by the foreign object determination device 1 in this embodiment is now explained with reference to FIG. 2. FIG. 2 is a flowchart showing the processing routine in determining the existence of a foreign object in the authentication target.

Foremost, when an authentication target is placed on the mounting region of the foreign object determination device 1, the light source unit 20 causes the authentication target to be irradiated with light, and the imaging unit 10 captures the authentication target twice by shifting the photography timing (step S101).

Subsequently, the image acquisition unit 31 acquires the two images captured in foregoing step S101 (step S102).

Subsequently, the finger region identification unit 32 compares the colors of the two images acquired in foregoing step S102 in pixel units, and identifies a difference pixel group (step S103).

Subsequently, the finger region identification unit 32 identifies a flesh color pixel group corresponding to the color of skin from the image that was first captured in foregoing step S101 (step S104).

Subsequently, the finger region identification unit 32 identifies the finger region by using the difference pixel group identified in foregoing step S103 and the flesh color pixel group identified in foregoing step S104 (step S105).

Subsequently, the region partitioning unit 33 partitions the finger region identified in foregoing step S105 into regions of mutually different colors by using the colors of the respective pixels contained in the finger region (step S106).

Subsequently, the foreign object determination unit 34 calculates a score showing the difference in color in comparison to the barycentric position for each pixel of the partitioned regions, and calculates the score for each partitioned region by adding up the calculated scores for each partitioned region (step S107).

Subsequently, the foreign object determination unit 34 determines whether the scores added up for each of the partitioned regions are greater than a predetermined value by which a foreign object is assumed to exist (step S108). When this determination is NO (step S108; NO), the foreign object determination unit 34 determines that a foreign object is not included in the authentication target (step S110).

Meanwhile, when it is determined in foregoing step S108 that the scores added up for each of the partitioned regions are greater than a predetermined value (step S108; YES), the foreign object determination unit 34 determines that a foreign object is included in the authentication target (step S109).

As described above, according to the foreign object determination device 1 of this embodiment, it is possible to determine whether a foreign object is included in the authentication target by identifying a finger region from an image in which an authentication target to be subjected to fingerprint authentication has been captured, partitioning the finger region into regions of mutually different colors, and using the colors and areas of the partitioned regions. Accordingly, it is possible to cancel the fingerprint authentication when a foreign object is included in the authentication target, and perform the fingerprint authentication when a foreign object is not included in the authentication target. Since it is thereby possible to appropriately perform fingerprint authentication based on a finger with no foreign object attached thereto, the accuracy of fingerprint authentication can be improved.

Note that each of the embodiments described above is merely an illustrated, and does not excluding the application of various modifications and technologies that are not specified in the embodiments. In other words, the present invention can be modified variously and implemented so as long as it does not deviate from the gist of the invention.

For example, while the image acquisition unit 31 of the foregoing embodiment captures the authentication target twice, the number of times that the image is to be captured is not limited to twice, and may also be once or three times or more. For example, if the image is to be captured once, the image acquisition unit 31 may comprise a stereo camera as the camera. As a result of capturing the image for foreign object determination with a stereo camera, the finger region identification unit 32 can identify the finger region from one image for foreign object determination. An example of the method of identifying the finger region in the foregoing case is now explained. For example, the shape of fingers and the shape of fingers with a foreign object are modeled in advance and stored in a database. The finger region identification unit 32 identifies the flesh color pixel group from the image for foreign object determination, and identifies the finger region by pattern-matching the flesh color pixel group and the models stored in the database.

Moreover, while the foreign object determination device 1 in the foregoing embodiment comprises the finger region identification unit 32, the configuration is not limited thereto. For example, when the imaging unit 10 is to capture a image of the authentication target without any background, there is no need to identify the finger region and, therefore, the finger region identification unit 32 is not required. In the foregoing case, the imaging unit 10 is disposed so that the finger and the foreign object attached to the finger are both included in the captured image, and the background is not included in the captured image.

Figure 3:
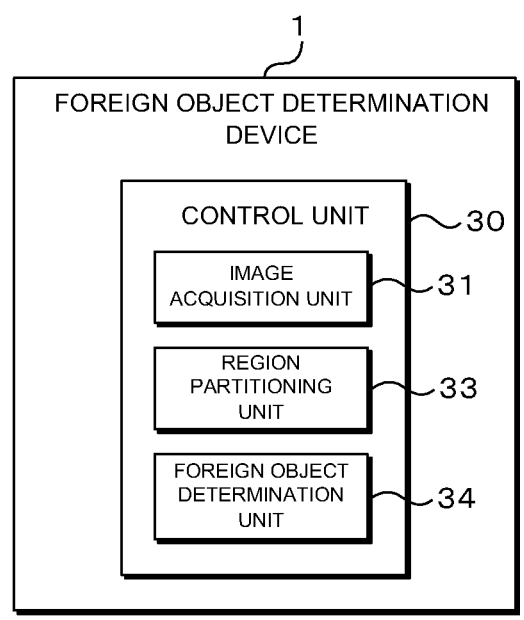
FIG. 3 is a block diagram illustrating the schematic configuration of the foreign object determination device in a modified example.

Moreover, while the foreign object determination device 1 in the foregoing embodiment comprises the imaging unit 10, the light source unit 20, the image acquisition unit 31, the finger region identification unit 32, the region partitioning unit 33, and the foreign object determination unit 34, all of these elements are not necessarily required. As shown in FIG. 3, the foreign object determination device 1 only needs to comprise at least the image acquisition unit 31, the region partitioning unit 33, and the foreign object determination unit 34. In the foregoing case, for example, the image acquisition unit 31 may acquire the image of the authentication target, which does not include the background, from the fingerprint authentication apparatus including the imaging unit 10 and the light source unit 20.

This application relates to and claims priority from Japanese Patent Application No. 2010-47585, filed on Mar. 4, 2010, the entire disclosure of which is incorporated herein by reference.

The foreign object determination device, the foreign object determination method and the foreign object determination program according to the present invention are suitable for improving the accuracy of fingerprint authentication.

1 . . . foreign object determination device, 10 . . . imaging unit, 20 . . . light source unit, 30 . . . control unit, 31 . . . image acquisition unit, 32 . . . finger region identification unit, 33 . . . region partitioning unit, 34 . . . foreign object determination unit.

What is claimed is:
1. A foreign object determination device, comprising:
an image acquisition unit for acquiring a plurality of images which capture a same authentication target before and after movement;
a finger region identification unit for identifying a finger region including a foreign object as a moving object from the images acquired by the image acquisition unit, by using a color of pixels in the image of the plurality of images representing the same authentication target and a difference of a color of a same pixel in the images of the plurality of images representing the same authentication target before and after movement acquired by the image acquisition unit;
a region partitioning unit for partitioning the finger region identified by the finger region identification unit into regions of mutually different colors by using predetermined determination criteria for determining differences in color; and
a foreign object determination unit for determining that the foreign object is included in the authentication target when a difference of colors in the regions, size of the regions and/or number of the regions, partitioned by the region partitioning unit, satisfies a predetermined condition.

2. The foreign object determination device according to claim 1,
wherein the foreign object determination unit calculates a score showing a difference between a color of a pixel of each of the regions partitioned by the region partitioning unit and a reference color of the image before the image has been partitioned, and determines whether a foreign object is included in the authentication target by using the score.

3. The foreign object determination device according to claim 2,
wherein the foreign object determination unit calculates the score for each pixel of the region and adds up the scores for each of the regions, and determines that a foreign object is included in the authentication target when the accumulated value is greater than a predetermined value by which a foreign object is assumed to exist.

4. The foreign object determination device according to claim 1, wherein the finger region identification unit compares, for each pixel in the images, the color of the same pixel in the images of the plurality of images representing the same authentication target before and after movement to obtain a difference of the color, compares the difference of the color with a predetermined threshold and identifies a pixel as a difference pixel when the difference of the color exceeds the threshold.

5. The foreign object determination device according to claim 4, wherein each pixel identified as a difference pixel is grouped into a difference pixel group.

6. The foreign object determination device according to claim 5, wherein the finger region identification unit compares, for each pixel in the image of the plurality of images representing the same authentication target, the color of the pixel with a predetermined skin color threshold range, wherein if the color of the pixel matches the predetermined skin color threshold range, the pixel is identified as a flesh color pixel.

7. The foreign object determination device according to claim 6, wherein each pixel identified as a flesh color pixel is grouped into a flesh color pixel group.

8. The foreign object determination device according to claim 7, wherein the finger region identification unit identifies the finger region using the difference pixel group and the flesh color pixel group.

9. A foreign object determination method, comprising:
acquiring a plurality of images which capture a same authentication target before and after movement;
identifying a finger region including a foreign object as a moving object from the images by using a color of pixels in the image of the plurality of images representing the same authentication target and a difference of a color of a same pixel in the images of the plurality of images representing the same authentication target before and after movement;
partitioning the finger region into regions of mutually different colors by using predetermined determination criteria for determining differences in color; and
determining that the foreign object is included in the authentication target when a difference of colors in the regions, size of the regions and/or number of the regions partitioned, satisfies a predetermined condition.

10. The foreign object determination method according to claim 9, wherein the identifying the finger region comprises:
comparing, for each pixel in the images, the color of the same pixel in the images of the plurality of images representing the same authentication target before and after movement to obtain a difference of the color;
comparing the difference of the color with a predetermined threshold; and
identifying a pixel as a difference pixel when the difference of the color exceeds the threshold.

11. The foreign object determination method according to claim 10, wherein each pixel identified as a difference pixel is grouped into a difference pixel group.

12. The foreign object determination method according to claim 11, wherein the identifying the finger region further comprises:
comparing, for each pixel in the image of the plurality of images representing the same authentication target, the color of the pixel with a predetermined skin color threshold range,
wherein if the color of the pixel matches the predetermined skin color threshold range, the pixel is identified as a flesh color pixel.

13. The foreign object determination method according to claim 12, wherein each pixel identified as a flesh color pixel is grouped into a flesh color pixel group.

14. The foreign object determination method according to claim 13, wherein the finger region is identified using the difference pixel group and the flesh color pixel group.

15. A non-transitory computer readable storage medium having a foreign object determination program for causing a computer to execute:
acquiring a plurality of images which capture a same authentication target before and after movement;
identifying a finger region including a foreign object as a moving object from the images by using a color of pixels in the image of the plurality of images representing the same authentication target and a difference of a color of a same pixel in the images of the plurality of images representing the same authentication target before and after movement;
partitioning the finger region into regions of mutually different colors by using predetermined determination criteria for determining differences in color; and
determining that the foreign object is included in the authentication target when a difference of colors in the regions, size of the regions and/or number of the regions partitioned, satisfies a predetermined condition.

* * * * *